United States Patent [19]

Murofushi et al.

[11] Patent Number: 5,994,107
[45] Date of Patent: *Nov. 30, 1999

[54] PROCESS OF PURIFYING XANTHAN GUM USING AN ALKALINE PROTEASE AND LYSOZYME

[75] Inventors: Kanji Murofushi; Taira Homma, both of Joetsu; Shigehiro Nagura, Niigata-ken, all of Japan; Richard Armentrout, La Jolla, Calif.

[73] Assignees: Shin-Etsu Chemical Co., Ltd., Tokyo, Japan; Shin-Etsu Bio, Inc., San Diego, Calif.

[ * ] Notice: This patent is subject to a terminal disclaimer.

[21] Appl. No.: 09/001,988

[22] Filed: Dec. 31, 1997

Related U.S. Application Data

[63] Continuation of application No. 07/990,758, Dec. 15, 1992, Pat. No. 5,705,368.

[30] Foreign Application Priority Data

Dec. 20, 1991 [JP] Japan ................................. 3-338244
Mar. 11, 1992 [JP] Japan ................................. 4-054898

[51] Int. Cl.⁶ ........................ C07C 1/02; C12N 1/00; C12N 9/00; C12P 19/06
[52] U.S. Cl. ...................... 435/104; 435/183; 435/252.1; 435/262; 435/822; 435/910
[58] Field of Search ................... 435/104, 114, 435/183, 252.1, 262, 822, 910

[56] References Cited

U.S. PATENT DOCUMENTS

| | | | |
|---|---|---|---|
| 3,591,578 | 7/1971 | Colin et al. | 260/209 |
| 3,966,618 | 6/1976 | Colegrove | 252/8.55 D |
| 4,010,071 | 3/1977 | Colegrove | 195/7 |
| 4,135,979 | 1/1979 | Corley et al. | 195/31 |
| 4,299,825 | 11/1981 | Lee | 424/180 |
| 4,567,140 | 1/1986 | Voelskow et al. | 435/42 |
| 4,720,389 | 1/1988 | Clare et al. | 426/329 |
| 4,729,900 | 3/1988 | Clare et al. | 426/329 |
| 5,079,348 | 1/1992 | Clare et al. | 536/3 |
| 5,153,317 | 10/1992 | Ortega et al. | 8/543 |
| 5,493,015 | 2/1996 | Murofushi et al. | 536/127 |
| 5,595,892 | 1/1997 | Murofushi et al. | 435/104 |
| 5,705,368 | 1/1998 | Murofushi et al. | 435/104 |

FOREIGN PATENT DOCUMENTS

| | | |
|---|---|---|
| 2606423 | 5/1988 | France . |
| 0129802 | 2/1978 | Germany . |
| 2060597 | 3/1990 | Japan . |
| 2085904 | 5/1982 | United Kingdom . |
| 2099008 | 12/1982 | United Kingdom . |

Primary Examiner—David M. Naff
Assistant Examiner—Deborah K. Ware
Attorney, Agent, or Firm—McAulay Nissen Goldberg Kiel & Hand, LLP

[57] ABSTRACT

Xanthan gum is purified by heat-treating a xanthan gum fermented broth, and consecutively treating the broth first with alkaline protease and then with lysozyme or in reverse order, and thereafter recovering xanthan gum from the treated broth. A clear aqueous solution of xanthan gum may be obtained without complex procedures. The xanthan gum is separated and purified and 0.3% aqueous solution of the purified xanthan gum has a transmittance of at least 80%.

8 Claims, No Drawings

PROCESS OF PURIFYING XANTHAN GUM USING AN ALKALINE PROTEASE AND LYSOZYME

The present application is a continuation of application Ser. No. 07/990,758, filed Dec. 15, 1992, now U.S. Pat. No. 5,705,368.

BACKGROUND OF THE INVENTION

1. Field of the Invention

The present invention relates to a process for the preparation of purified xanthan gum, and more particularly to a process for the improvement in transparency of fermented broth and aqueous solution of xanthan gum by enzymatic treatment.

2. Description of the Related Art

Xanthan gum can be obtained by a well-known fermentation process. It is recovered by precipitation with isopropanol from a fermented broth of a xanthan gum-producing bacterium, e.g., *Xanthomonas campestris* a species in the genus Xanthomonas. (This compound and process for preparing it are described in U.S. Pat. No. 3,659,026, col. 4.)

Other processes for the manufacture of xanthan gum use, in place of *Xanthomonas campestris*, such other known xanthan gum-producing bacteria as *Xanthomonas carotate, incanae, begoniae, papavericola, translucens, vasculorum,* and *hederae*. All these species can produce a xanthan gum fermented broth.

The broth at the end of fermentation contains from 0.5 to 2 percent by weight of undissolved matter including unconsumed nutrients and bacterial cell residues, besides about 2 to 5 percent by weight of xanthan gum. Naturally, an aqueous solution of solid xanthan gum separated by extraction from the broth has very low transparency. This presents problems in the fields where clear products are required, such as food and cosmetic industries, and in applications for secondary recovery of petroleum.

For the purification of xanthan gum, methods that depend on centrifugation or cake filtration for the removal of the undissolved matter from the broth are commonly known. In either case, however, the broth is so viscous that it needs dilution with water and concentration, and the cost and operation of these additional steps make the methods impractical. A variation of those methods suggests heating of the broth to enhance its filtration properties.

One effective approach is solubilizing the undissolved matter in the broth by enzymatic treatment. Many proposals have hitherto been made in this direction.

For example, U.S. patent application Ser. No. 449,875 of 1974 (Japanese Patent Provisional Publication (Kokai) No. 50-121493) and U.S. patent applications Ser. Nos. 513,810/1974, 3,966,618/1976, 4,010,071/1977, and 416,525/1979 propose clarification by use of alkaline protease and neutral protease. They report in fact, that xanthan gum solutions cannot necessarily be made quartz-crystalline clear and there remains certain turbidity in the solutions. Thorough transparency is yet to be attained.

British Patent Application No. 8,132,564/1981 (Japanese Patent Kokai No. 58-81792) teaches the use of acidic protease and neutral protease. U.S. patent application Ser. No. 797,093/1977 (Japanese Patent Kokai No. 62-44918) teaches bringing a solution that results from protease treatment into contact with a siliceous solid matter and then removing cell bodies from an aqueous polymer solution. French Patent Application No. 8,110,403/1981 (Japanese Patent Kokai No. 57-202303) proposes an enzymatic treatment using polysaccharase and protease. U.S. Pat. No. 4,431,734 (Japanese Patent Kokai No. 63-287494) teaches combined use of a polygalacturonase-active enzyme and a protease-active enzyme. U.S. patent application Ser. No. 147,812/1980 (Japanese Patent Kokai No. 57-5698) proposes the adoption of a composite enzyme having both β-1,3-glucanase- and protease-activities. None of the proposed treatments with protease have however, proved satisfactorily effective.

Among other enzymatic processes so far proposed are the utilization of a nuclease-active enzyme according to British Patent Application No. 8,431,653/1984 (Japanese Patent Kokai No. 61-146193) and the purification by the action of cellulase according to French Patent Application No. 8,021,395/1980 (Japanese Patent Kokai No. 57-91194). They too have failed to be adequately effective.

Japanese Patent No. 1318520 (Japanese Patent Kokai No. 60-44919) introduces a treatment with the simultaneous addition of lysozyme, N-acetylmuramyl-L-alanine amidase, and peptidase. These enzymes are known to be able to lyse cell walls, but they have only slight action directly on Gram-negative bacteria. Despite long treatment time required, their effect is disappointingly low.

As summarized above, there have been known methods for removing water-insoluble microbial residues and culture medium-derived undissolved matter, including the methods relying upon centrifugation or cake filtration or upon enzymatic treatment to make the undissolved matter soluble in water. With those methods, however, it has been difficult to obtain a xanthan gum fermented broth with a high degree of transparency.

SUMMARY OF THE INVENTION

In view of the technical problems described, this invention is aimed at the clarification of a xanthan gum fermented broth.

Thus, an object of the present invention is to provide a process for the preparation of xanthan gum having excellent viscosity properties by the steps of heat-treating a xanthan gum fermented broth under specific pH and temperature conditions, uninterruptedly treating the broth enzymatically, and thereafter separating solid xanthan gum by extraction from the treated broth using a specific organic solvent, e.g., isopropyl alcohol, so that an aqueous solution of 0.3 percent by weight of the solid xanthan gum may have a transmittance of at least 80 percent.

The invention provides a method for obtaining a highly transparent aqueous solution of xanthan gum by heat-treating a xanthan gum fermented broth as a pretreatment for enzymatic treatment, cooling, and, uninterruptedly, treating the broth first with alkaline protease and then with lysozyme or in reverse order, thereby fully solubilizing water-insoluble bacterial cell residues and culture medium-derived undissolved matter.

In other words, the invention thus provides a process for preparing highly transparent fermented xanthan gum by a heat treatment at an initial pH of at least 9 and an immediately ensuing enzymatic treatment in which alkaline protease and lysozyme are combined to thoroughly solubilize water-insoluble bacterial cell residues and culture medium-derived undissolved matter, without adversely affecting the viscosity properties characteristic of xanthan gum.

The heat treatment can be performed at an initial pH of from 9 to 12.5, preferably from 10 to 12, and at a temperature of from 45 to 70° C., preferably from 50 to 60° C., for at least 30 minutes. If the pH is below 9 the bacterial solubilization sometimes does not proceed efficiently, leading to unfavorable results. If it is above 12.5 the broth could be colored or the viscosity properties of the product impaired. Although the pH naturally decreases during the course of the treatment, it should preferably be maintained above 8. Any temperature below 45° C. is undesirable because it may hamper efficient solubilization of bacteria in the enzymatic treatment. A temperature above 70° C. is again undesirable because it can cause coloring of the broth or adverse effects upon the viscosity properties of the product. Treatment for no less than 30 minutes gives a sufficient effect, but a treatment time of more than 2 hours is not advisable since it can decrease the productivity. The heat treatment must precede the enzymatic treatment. Without this pretreatment the enzymatic treatment would not be effective or take a prolonged time period before it proves effective.

The enzymatic treatment is carried out in two steps using alkaline protease and lysozyme. The duration of each treatment step is desirably between 20 minutes and 5 hours. A period shorter than 20 minutes is not desirable in that the treatment effect is not fully achieved. Treatment for more than 5 hours would not bring any additional treatment effect, leading to reduced productivity.

Treatment with alkaline protease is conducted at a pH in the range from 6.0 to 10.0, preferably from 7.5 to 9.0, at a concentration of 10 to 500 ppm, and at a temperature of 40 to 65° C. for at least 20 minutes. A temperature below 40° C. is not recommended from the viewpoint of productivity because lowered enzymatic activity would call for a treating time of more than 6 hours. A temperature above 65° C. would deactivate the enzyme, making the treatment noneffective. Acidity below pH 6.0 would deactivate alkaline protease, while a pH above 10.0 is also undesirable since it can deteriorate the physical properties of the product. If the concentration is below 10 ppm a satisfactory effect would not result despite extension of the treating time. Conversely a concentration in excess of 500 ppm is not advisable because of higher production costs; an excessive concentration does not produce any further improvements.

Treatment with lysozyme is done at a pH value in the range of 5.5 to 8.0, preferably between 6.5 and 7.5, a concentration of 0.5 to 100 ppm, and a temperature of 25 to 45° C. for at least 20 minutes. A temperature above 45° C. is undesirable because it can lower the activity of lysozyme in some cases. At a pH above 8 lysozyme would not be active and, below 5.5 the physical properties of the product could deteriorate. If the concentration is less than 0.5 ppm prolonged treatment would become necessary, and even if treatment time is prolonged it may not lead to any meaningful effects. A concentration of more than 100 ppm is not warranted from an economical standpoint. Any of the two enzymatic treatment steps may precede the other.

Enzymes useful for the reduction of the invention to practice are: an alkaline protease produced by a bacterium in the genus Bacillus, such as B. subtilis and a lysozyme known as endo-β-1,4-N-acetylhexosaminidase which hydrolyzes the β-1,4 bonds of N-acetylglucosamine and N-acetylmuramic acid in bacterial cell walls. Generally, alkaline proteases produced by B. licheniformis, B. amylaliquifaciens, and B. pumilis are known besides that which originates from B. subtilis. As for lysozymes, there are known animal lysozymes, such as egg white lysozymes of chickens, ducks, quails, turkeys, and geese, spleen lysozymes of dogs and rats, and lysozymes present in human urine (of leukemia patients), human milk, and tears. Plant lysozymes have been found in turnips, cabbages, and papaya juice. For the present invention, however, the origins of the enzymes are of little importance.

The process according to the invention permits the omission of such complex process steps as dilution, cake filtration, and concentration that have hitherto been required for the removal of undissolved matter. This brings ease of operation and economical advantage. A further advantage is high transparency of the product that ordinary enzymatic processes have failed to realize.

DETAILED DESCRIPTION OF THE PREFERRED EMBODIMENT

The invention will now be described concretely in connection with its examples and comparative examples.

EXAMPLE 1

| I. Preproduction medium | | II. Production medium | |
|---|---|---|---|
| Glucose | 5.8 g/l | Glucose | 58 g/l |
| Polypeptone | 5.2 " | Polypeptone | 2 " |
| Yeast extract | 2.6 " | $KH_2PO$ | 2 " |
| NaCl | 9 " | $MgSO_4 \cdot 7H_2O$ | 0.5 " |
| Water | 1.8 l | Water | 16.2 l |

A medium of composition II was placed in a 30-liter fermenter and inoculated with a Xanthomonas campestris broth that had been cultured for 24 hours on a medium of composition I. It was then cultured under aeration and agitation at pH 6.5 to 7.0 and at 30° C. for two days, and a broth containing 30 g xanthan gum per liter was obtained. With stirring the broth was heat-treated at an initial pH of 11 and at 55° C. for 90 minutes and, while being kept at 55° C. the broth was adjusted to pH 8.5 and, after the addition of 300 ppm alkaline protease ("Bioplase", a product of Nagase Biochemical Co.), the mixture was treated with stirring at 55° C. for two hours. Next, the resulting broth was cooled down to 35° C., 3 ppm lysozyme ("Lysozyme Taiyo", a product of Taiyo Chemical Co.) was added, and the mixture was further treated with stirring at 35° C. for one hour.

EXAMPLE 2

A broth prepared in the same way as described in Example 1 was enzymatically treated in the reverse order. After cooling, it was adjusted to pH 7.0 and, with the addition of 3 ppm lysozyme ("Lysozyme Taiyo" of Taiyo Chemical), the mixture was treated with stirring at 35° C. for two hours. Next, the broth was heated to 55° C., 300 ppm alkaline protease ("Bioplase" of Nagase Biochemical) was added, and the mixture was treated with stirring at 55° C. for one hour.

For the purposes of analysis, the broth was sampled after each of the process steps, i.e., after the conclusion of fermentation, the heat treatment, and the first and second stages of enzymatic treatment. Xanthan gum was separated by extraction from the test broth using 1.6 times by weight of isopropyl alcohol, and the extract was air dried. An aqueous solution containing 0.3 percent by weight of the thus obtained solid xanthan gum was prepared, and the sample was tested for light transmittance and viscosity (with a Brookfield viscometer at 30 rpm). Table 1 summarizes the results.

TABLE 1

|  | Example 1 | | Example 2 | |
| --- | --- | --- | --- | --- |
| Process step | Transmittance | Viscosity | Transmittance | Viscosity |
| After fermentation | 11% | 290 cp | 12% | 300 cp |
| After heat treatment | 18 | 290 | 20 | 290 |
| 1st stage enzymatic treatment | 65 | 300 | 62 | 300 |
| 2nd stage enzymatic treatment | 94 | 305 | 94 | 300 |

EXAMPLES 3 AND 4

The procedure of Example 1 was repeated for treatments except that the lysozyme concentration was varied. The results are given in Table 2.

TABLE 2

|  | Example 3 Lysozyme 30 ppm | | Example 4 Lysozyme 1 ppm | |
| --- | --- | --- | --- | --- |
| Process step | Transmittance | Viscosity | Transmittance | Viscosity |
| After fermentation | 11% | 280 cp | 12% | 300 cp |
| After heat treatment | 18 | 290 | 20 | 295 |
| 1st stage enzymatic treatment | 65 | 290 | 65 | 310 |
| 2nd stage enzymatic treatment | 97 | 290 | 90 | 300 |

EXAMPLE 5

Fermentation performed in the same manner as in Example 1 yielded a broth containing 30 g xanthan gum per liter. With stirring, the broth at an initial pH of 7.0 was heat-treated at 80° C. for 90 minutes and then cooled to and kept at 55° C. After the cooling the pH was adjusted to 8.5, and 300 ppm alkaline protease ("Bioplase" of Nagase Biochemical) was added, and the mixture was treated with stirring at 55° C. for two hours. Next, the broth was cooled down to 35° C. and, after the addition of 3 ppm lysozyme ("Lysozyme Taiyo" of Taiyo Chemical), the mixture was treated with stirring at 35° C. for one hour.

For analysis, the broth was sampled after each of the process steps, i.e., after the conclusion of fermentation, the heat treatment, and the first and second stages of enzymatic treatment. Xanthan gum was separated by extraction from the test broth using 1.6 times by weight of isopropyl alcohol, and the extract was air dried. An aqueous solution containing 0.3 percent by weight of the thus obtained solid xanthan gum was prepared, and the sample was tested for light transmittance and viscosity (with a Brookfield viscometer at 30 rpm). Table 3 shows the results.

TABLE 3

|  | Example 5 | |
| --- | --- | --- |
| Process step | Transmittance | Viscosity |
| After fermentation | 11% | 290 cp |
| After heat treatment | 8 | 275 |
| 1st stage enzymatic treatment | 46 | 300 |
| 2nd stage enzymatic treatment | 90 | 305 |

Comparative Examples 1 and 2

Fermentation and heat treatment were carried out in a manner similar to Example 1, and either lysozyme or alkaline protease alone was used in enzymatic treatment. The conditions for treatment with either enzyme were the same as used in Example 1. After each test period xanthan gum was separated from the resulting broth by extraction with 1.6 times by weight of isopropyl alcohol and the extract was air dried. An aqueous solution containing 0.3 percent by weight of the xanthan gum so obtained was prepared and tested for light transmittance and viscosity. As Table 4 indicates, the solutions thus prepared failed to attain, despite extended treating periods, the high transparency that the process of the present invention achieves.

TABLE 4

|  | Comparative Example 1 Lysozyme | | Comparative Example 2 Alkaline protease | |
| --- | --- | --- | --- | --- |
| Treating time | Transmit'nce | Viscosity | Transmit'nce | Viscosity |
| Untreated | 35% | 290 cp | 35% | 290 cp |
| 2 hrs | 60 | 300 | 62 | 300 |
| 4 " | 62 | 300 | 65 | 300 |
| 6 " | 64 | 300 | 69 | 300 |

Comparative Example 3

In the manner described in Example 1, fermentation and heat treatment were performed, with the exception that the enzymatic treatment used lysozyme and alkaline protease together. The reaction conditions were pH 7.5 and 45° C. at which both enzymes were active. With the addition of 300 ppm Bioplase and 3 ppm lysozyme, the reaction was carried out for 6 hours. After each treating time the sample was tested for light transmittance and viscosity as was the case with Comparative Example 1. The results are given in Table 5.

TABLE 5

|  | Comparative Example 3 | |
| --- | --- | --- |
| Treating time | Transmittance | Viscosity |
| Untreated | 35% | 290 cp |
| 2 hrs | 63 | 310 |

TABLE 5-continued

| | Comparative Example 3 | |
|---|---|---|
| Treating time | Trans- mittance | Viscosity |
| 4 | 65 | 310 |
| 6 | 69 | 310 |

Comparative Example 4

The fermentation of Example 1 was directly by the two-stage enzymatic treatment without the heat treatment. Samples of the individual process steps were tested for light transmittance and viscosity. Table 6, which shows the results, indicates that the omission of heat treatment reduced the enzymatic effects of the resulting broths.

TABLE 6

| | Comparative Example 4 | |
|---|---|---|
| Process step | Trans- mittance | Viscosity |
| After fermentation | 11% | 300 cp |
| 1st stage enzymatic treatment | 40 | 310 |
| 2nd stage enzymatic treatment | 60 | 310 |

We claim:

1. A process for the preparation of purified xanthan gum comprising the steps of heat-treating a fermented broth containing xanthan gum, and successively treating the broth first with alkaline protease and then with lysozyme, thereafter, separating solid xanthan gum by extraction from the treated broth using an organic solvent such that 0.3% aqueous solution of the purified xanthan gum has a transmittance of at least 80%.

2. A process for the preparation of purified xanthan gum, comprising the steps of heat-treating a fermented broth of xanthan gum, and successively treating the broth first with lysozyme and then with alkaline protease and recovering purified xanthan gum from the treated broth such that 0.3% aqueous solution of the purified xanthan gum has a transmittance of at least 80%.

3. The process of claims 1 or 2 wherein the recovered purified xanthan gum has a transmittance of 90%.

4. The process as claimed in claim 1 or 2, wherein the heat treatment is carried out with an initial pH of 9 to 12.5 at a temperature of 45 to 70° C. for at least 30 minutes.

5. The process as claimed in claim 4, wherein the treatment with alkaline protease is carried out with the addition of 10 to 500 ppm of alkaline protease to the fermented broth of xanthan gum, at a temperature of 40 to 65° C. and a pH of 6.0 to 10.0 for at least 30 minutes.

6. The process as claimed in claim 1 or 2, wherein the treatment with alkaline protease is carried out with the addition of 10 to 500 ppm of alkaline protease to the xanthan gum fermented broth, at a temperature of 40 to 65° C. and a pH of 6.0 to 10.0 for at least 30 minutes.

7. The process as claimed in claim 1 or 2, wherein the treatment with lysozyme is carried out with the addition of 0.5 to 100 ppm of lysozyme to the fermented broth of xanthan gum, at a temperature of 25 to 45° C. and a pH of 5.5 to 8.0 for at least 30 minutes.

8. The process as claimed in claim 4, wherein the treatment with lysozyme is carried out with the addition of 0.5 to 100 ppm of lysozyme to the fermented broth of xanthan gum, at a temperature of 25 to 45° C. and a pH of 5.5 to 8.0 for at least 30 minutes.

* * * * *

UNITED STATES PATENT AND TRADEMARK OFFICE
CERTIFICATE OF CORRECTION

Patent No.: 5,994,107

Issued: November 30, 1999

Inventor(s): Kanji MUROFUSHI, et al.

It is certified that this error appears in the above-identified patent and that said Letters Patent is hereby corrected as shown below:

TITLE PAGE
The filing date of the second priority application should read as follows:

[30]  Foreign Application Priority Data

Dec. 20, 1991  [JP]  Japan  .................................. 3-338244
Mar. 13, 1992  [JP]  Japan  .................................. 4-054898

Signed and Sealed this

Fifth Day of September, 2000

Attest:

Q. TODD DICKINSON

Attesting Officer

Director of Patents and Trademarks